(12) United States Patent
France

(10) Patent No.: US 7,190,176 B2
(45) Date of Patent: Mar. 13, 2007

(54) ANALYSIS OF VARIABLE-DEPTH SAMPLE USING A SWEEPING MICROWAVE SIGNAL

(75) Inventor: Garry George France, Queensland (AU)

(73) Assignee: Callidan Instruments PTY Ltd (AU)

( * ) Notice: Subject to any disclaimer, the term of this patent is extended or adjusted under 35 U.S.C. 154(b) by 33 days.

(21) Appl. No.: 10/528,549

(22) PCT Filed: Sep. 25, 2003

(86) PCT No.: PCT/AU03/01270

§ 371 (c)(1),
(2), (4) Date: Mar. 21, 2005

(87) PCT Pub. No.: WO2004/029600

PCT Pub. Date: Apr. 8, 2004

(65) Prior Publication Data

US 2005/0253595 A1    Nov. 17, 2005

(30) Foreign Application Priority Data

Sep. 26, 2002   (AU) ............................. 2002951784

(51) Int. Cl.
   *G01R 27/04*   (2006.01)
   *G01N 5/02*    (2006.01)
(52) U.S. Cl. ............................ 324/639; 324/640; 73/73
(58) Field of Classification Search ................ 324/639, 324/640; 73/73
   See application file for complete search history.

(56) References Cited

U.S. PATENT DOCUMENTS

| | | | |
|---|---|---|---|
| 4,788,853 A | 12/1988 | Bell | |
| 5,132,623 A * | 7/1992 | De et al. | 324/338 |
| 5,315,258 A * | 5/1994 | Jakkula et al. | 324/640 |
| 5,648,038 A | 7/1997 | Fathi et al. | |
| 6,107,809 A | 8/2000 | Moshe et al. | |
| 6,560,562 B2 * | 5/2003 | Gould | 702/181 |
| 2002/0198863 A1 * | 12/2002 | Anjur et al. | 707/1 |

FOREIGN PATENT DOCUMENTS

| | | |
|---|---|---|
| AU | B-61689/90 | 4/1991 |
| GB | 2 122 741 A | 1/1984 |
| GB | 2 211 299 A | 6/1989 |
| GB | 2 230 099 A | 10/1990 |
| GB | 2 359 630 A | 8/2001 |

* cited by examiner

*Primary Examiner*—Anjan Deb
*Assistant Examiner*—Jeff Natalini
(74) *Attorney, Agent, or Firm*—Fitch, Even, Tabin & Flannery

(57) ABSTRACT

An apparatus and method for analysing an amount of at least one component in a sample (21) by measuring a microwave signal (13) that has passed at least partially through the sample (21), the apparatus comprising: a microwave generator that generates a continuous linear sweeping microwave signal varying in frequency, a microwave transmitter (11), a microwave receiver (12), at least one microwave analyser that analyses phase shift and/or change in amplitude of a transmitted and received signal (13), a (40) for determining a depth of the sample (21) and a processor that determines the amount of the component(s) in the sample (21) from the microwave analyser.

26 Claims, 6 Drawing Sheets

ANALYSIS OF VARIABLE-DEPTH SAMPLE USING A SWEEPING MICROWAVE SIGNAL

FIELD OF THE INVENTION

THIS INVENTION relates to an apparatus, use thereof and method for determining an amount of a component in a sample by measuring a microwave signal transmitted through the sample. The invention is suitable for determining an amount of a component in a sample located on a moving conveyor belt wherein the sample may vary in depth.

BACKGROUND OF THE INVENTION

On-line analysis for total moisture of a material is critical to enable a process technician and/or plant operator to optimize processes for a wide range of applications, such as dust suppression, process control, achieving product specifications and material handling.

Moisture measurement using microwave methods are based is upon a relatively high dielectric constant of water in comparison to a dielectric property of a material to be analysed. When a microwave signal passes through the material, some of the signal is absorbed such that the amplitude (ie. power level) of the microwave signal is less at a receiver than that transmitted. An amount of attenuation of this signal is related directly to the dielectric constant of the analysed material.

To illustrate this method, common sand (silicon dioxide) has a dielectric constant of 4.2 and water has a dielectric constant of 80.4. A variable amount of water within the sand results in a large variation in the combined dielectric constant of the sand and water, which is then measurable by detecting a change in the microwave signal.

In addition to monitoring attenuation, velocity of the microwave signal is also effected by the dielectric constant of the material to be analysed with and without water. Increases in the dielectric constant slows the velocity of the microwave signal as it passes through the analysed material. This slowing of microwave velocity is proportional to a phase shift in microwave signal. Accordingly, velocity may be determined by measuring phase shift of the microwave signal.

GB 2,122,741 describes an apparatus for monitoring crushed coal. The apparatus monitors ash content and moisture content of the coal by respectively transmitting and detecting X-ray and microwave radiation. The microwave radiation amplitude is chopped at a low frequency of about 1.0 KHz, which is suitable for analysing a crushed sample such as coal. However, this apparatus is not well suited for determining moisture content of is other types of samples by on-line sampling methods.

U.S. Pat. No. 4,788,853 describes a moisture meter that also uses microwave signals at discrete discontinuous frequencies. This patent states that the number of frequencies required to perform the invention is not critical as long as sufficient data is generated.

AU 61689/90 describes an apparatus for determining moisture content in a sample of varying thickness on a conveyor belt. The microwave signals are also transmitted at discrete discontinuous frequencies within a selected range.

Although the above described apparatus may be useful for determining moisture content in a sample, these apparatus are nevertheless still prone to substantial errors or inaccuracies due at least in part to variation in sample depth or configuration. Also, transferring microwave technology to an on-line situation such as a conveyor belt poses many challenges.

SUMMARY OF THE INVENTION

It is an object of the invention to provide an alternative or improvement to the abovementioned prior art.

In one aspect, the invention provides a sample analysis apparatus that measures an amount of at least one component in a sample comprising:

(i) a microwave generator that generates a continuous linearly sweeping microwave signal varying in frequency;

(ii) a microwave transmitter that transmits the generated signal;

(iii) a microwave receiver that receives the transmitted signal;

(iv) at least one microwave analyser that generates an output signal that is operatively connected to the microwave generator and to the microwave receiver; said output signal indicating phase and/or amplitude differences between the generated signal and the received signal;

(v) means for determining a depth of the sample located between said microwave transmitter and said microwave receiver; and (vi) a processor that determines the amount of said at least one component in said sample from said depth and said output signal.

Preferably, the means for determining a depth of the sample comprises a sample depth analyser that measures depth of the sample.

More preferably, the sample depth analyser is an ultrasonic transmitting device.

Preferably, the respective microwave transmitter and receiver comprise respective antennas.

In one form, the microwave analyser comprises a microwave mixer that measures phase shift by receiving a portion of the transmitted signal and a portion of the received signal.

In another form, the microwave analyser comprises a microwave amplitude detector that measures an amplitude of the received signal.

In still another form, the microwave analyser comprises both a microwave mixer and microwave amplitude detector.

Preferably, phase shift and/or attenuation of the amplitude of the microwave signal is measured by random stratified sampling of the received signal.

Preferably, the processor is a microprocessor.

The sample may be water, ore, carbon, salt, fat or protein.

An amount of water in the sample may be determined using the equation:

Moisture content=$M0+M1$*(Attenuation/Depth of sample)+$M2$*(Velocity/Depth of sample)+$M3$*(Velocity/Depth of sample)$^2$+$M4$*(Attenuation/Depth of sample)$^2$; wherein Attenuation=(amplitude measured with sample)−(amplitude measured without sample);

Velocity=(microwave velocity measurement with sample)−(microwave velocity measurement without sample); and Depth of sample=(Depth with sample)−(depth without sample); and $M0$, $M1$, $M2$, $M3$ and $M4$ are calibration coefficients determined by performing a simple linear regression of variables: (Attenuation/Depth of sample), (Velocity/Depth of sample), (Velocity/Depth of sample)$^2$ and (Attenuation/Depth of sample)$^2$ against experimentally determined values for the component.

In another aspect the invention provides use of the apparatus to determine an amount of at least one component in a sample.

In a further aspect, the invention provides a method for measuring an amount of at least one component in a sample including the steps of:

(1) generating a continuous linearly sweeping microwave signal varying in frequency;

(2) transmitting the generated signal;

(3) receiving a received signal;

(4) measuring and analysing the generated signal and the received signal and generating an output signal; said output signal indicating phase and/or amplitude differences between the generated signal and the received signal;

(5) measuring a depth of the sample to provide a sample depth measurement; and (6) processing the output signal and the sample depth measurement to determine the amount of the component in the sample.

Preferably, for the abovementioned aspects the continuous linearly sweeping microwave signal varies in frequency between a range of about 0.10 GHz to 4.00 GHz.

More preferably, the continuous linearly sweeping microwave signal varies in frequency between a range inclusive of 1.25 GHz to 1.65 GHz.

It will be appreciated that the present invention provides an improved apparatus and method for measuring one or more components of a sample by transmitting and receiving a continuous linearly sweeping microwave signal. The invention also provides in a preferred form a unique is means of sampling the amplitude (eg. microwave power level) and/or phase shift (eg. microwave velocity) by random stratified sampling such that errors introduced by varying bulk density and bed depth of the sample are less influential upon the result. Accordingly, accuracy of the measured component(s) of the sample (eg. crushed or uncrushed) may be improved by using the invention. It will also be appreciated that the invention may be used to measure one or more components of any suitable sample or material, wherein the component(s) is penetrable by a microwave signal, and is preferably capable of changing or modifying the amplitude and/or velocity (which results in a phase shift) in a transmitted microwave signal when compared with a received microwave signal after passing through the sample.

It will be appreciated that the linear sweeping microwave measurement cycle may ensure that the measurement is in fact continuous and no material within the analysis zone goes unmeasured. Accordingly, the invention is suitable for on-line applications such as analyzing moisture content of samples moving on a conveyor belt.

Throughout this specification unless the context requires otherwise, the word "comprise", and variations such as "comprises" or "comprising", will be understood to imply the inclusion of the stated integers or group of integers or steps but not the exclusion of any other integer or group of integers.

DESCRIPTION OF THE DRAWINGS AND TABLES

In order that the invention may be readily understood and put into practical effect, preferred embodiments will now be described by way of example with reference to the accompanying drawings wherein like reference numerals refer to like parts and wherein:

FIG. 1A shows an end view of a general configuration of an apparatus for measuring an amount of a component in a sample on a conveyor belt;

FIG. 1B shown a side view of the apparatus in FIG. 1;

Figure 5:
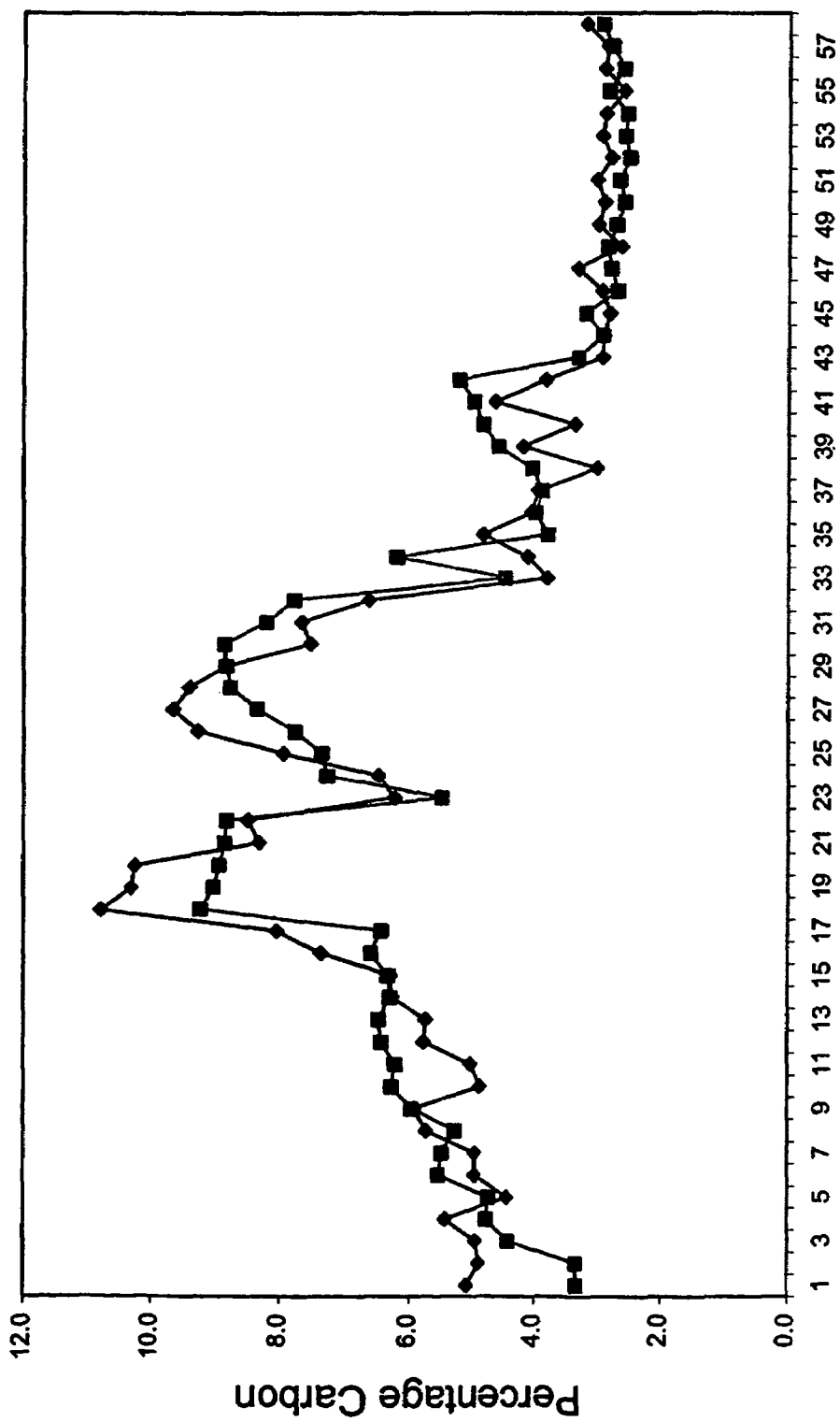
Figure 6:
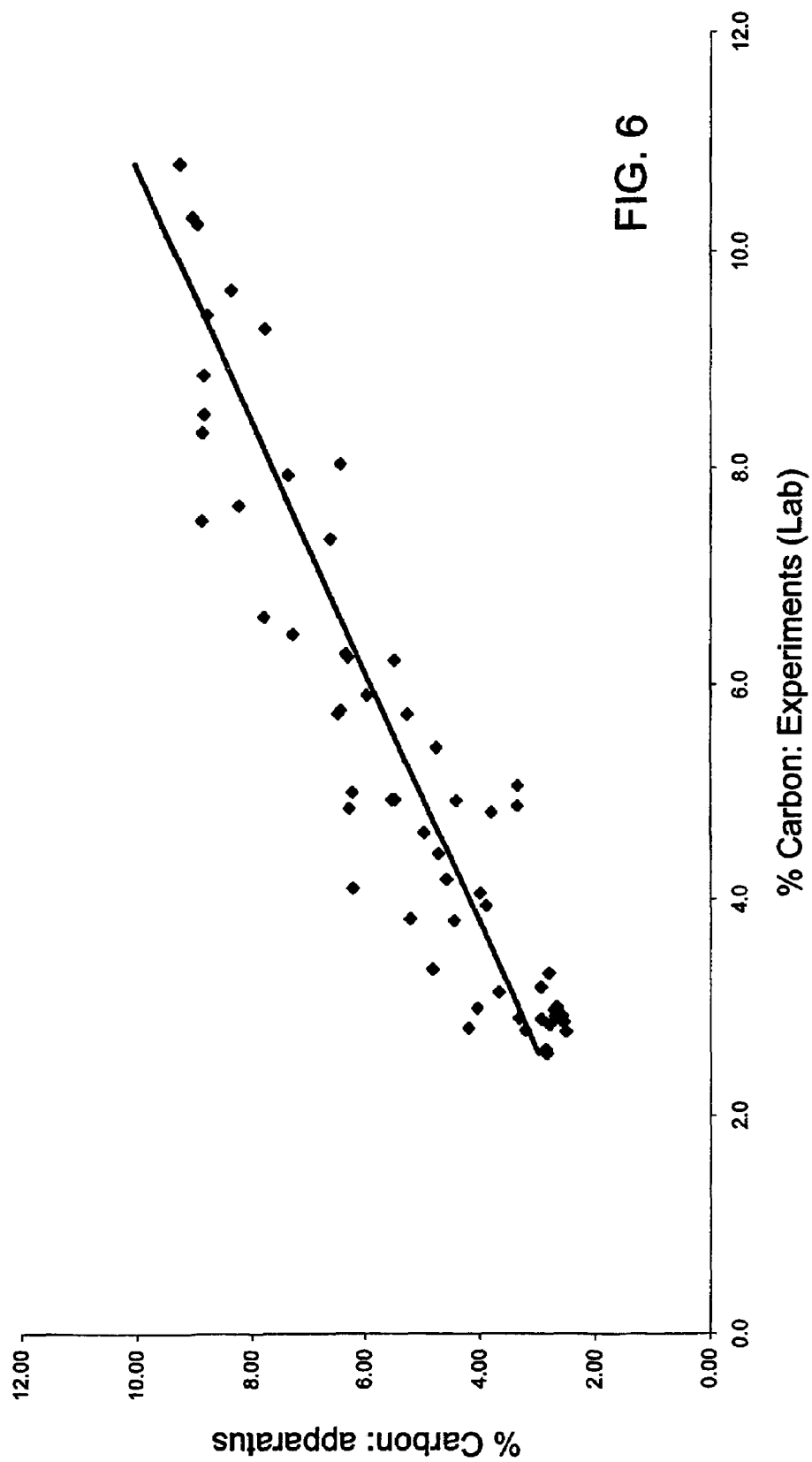

FIG. 5 graphically illustrates the data in relation to percent carbon in flyash shown in table 5, laboratory experimental data is shown as diamonds (♦) and the data determined by the invention is shown as squares (□);

FIG. 6 is a graph of data comparing percent carbon determined by laboratory experimentation versus percent carbon determined by using the apparatus of the invention;

TABLE 1: measured sample variables, percent water determined experimentally (lab) and percent water predicted using of the apparatus of the invention (gauge) for sugar;

TABLE 2: output data from a simple linear regression of data in table 2;

TABLE 3: measured sample variables, percent water determined experimentally and percent water predicted using of the apparatus of the invention for peanut samples and regression output;

TABLE 4: output data from a simple linear regression of data in table 3; and

TABLE 5: data comparing percent carbon determined by laboratory experimentation and determined by using the apparatus of the invention.

DETAILED DESCRIPTION OF THE INVENTION

The present invention relates to an apparatus, use thereof and method for measuring and determining an amount of a component in a sample. The amount of the component is preferably determined as a percentage of a total amount of the sample, but the amount may also be determined as an actual amount, eg by determining weight, volume, etc. Preferred uses of the invention are described herein in relation to respectively measuring water (eg moisture content) and carbon in flyash in a sample. It will be appreciated that the invention is not limited to measuring only water and carbon, and other suitable components of the sample may be measured as determined by a person skilled in the art.

It will also be appreciated that in one embodiment of the invention, one or more components may be measured simultaneously (ie concurrently) or in series by analyzing the microwave signals accordingly. In such an embodiment the processor may determine an amount of each selected component in the sample using an equation specific for the particular component. The equation may include calibration coefficients determined for the selected component and selected sample.

The term "component" refers to any constituent or part of a sample, for example a specific element or compound such as water, carbon, salt, fat, protein or any other component that is preferably capable of modifying a microwave signal, for example by changing the amplitude and/or velocity in a transmitted microwave signal when compared with a signal received after passing through the sample.

The term "free" moisture content as used herein means water molecules within a material that are able to rotate freely within the material.

"Sample" also refers to "material", which includes any suitable substance, for example ores and minerals such as coal, flyash, nickel ore, alumina; chromium ore, wood chips; products including, bulk foods, textiles, chemicals, foodstuff, processed foods, sugar, pasta, coffee, peanuts, wheat, barley, beef jerky, kitty litter, paper, polystyrene, plastics, and any other substance that is penetrable by microwaves. The sample comprises the component being analysed.

Figure 1A:
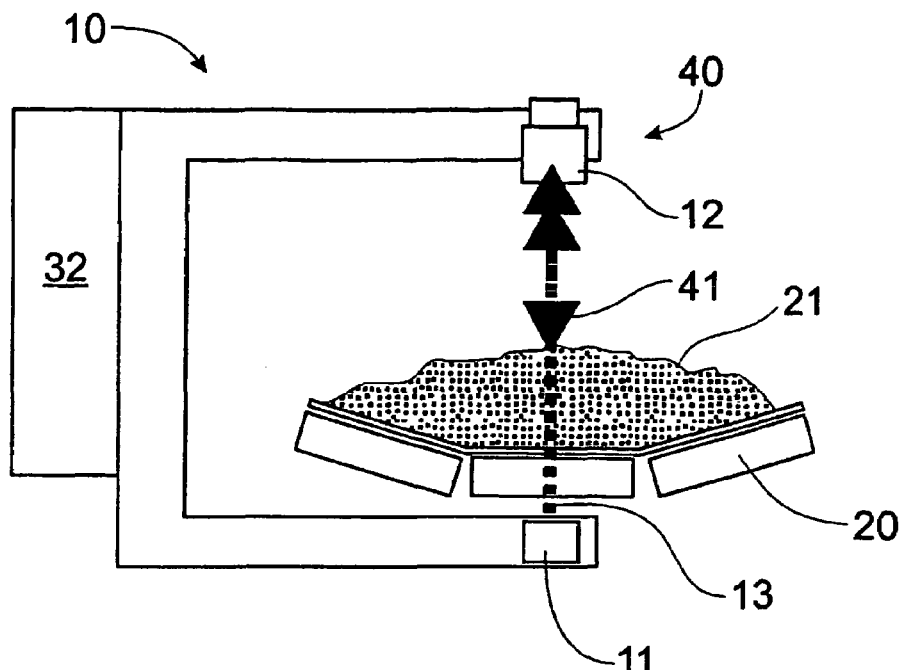
Figure 1B:
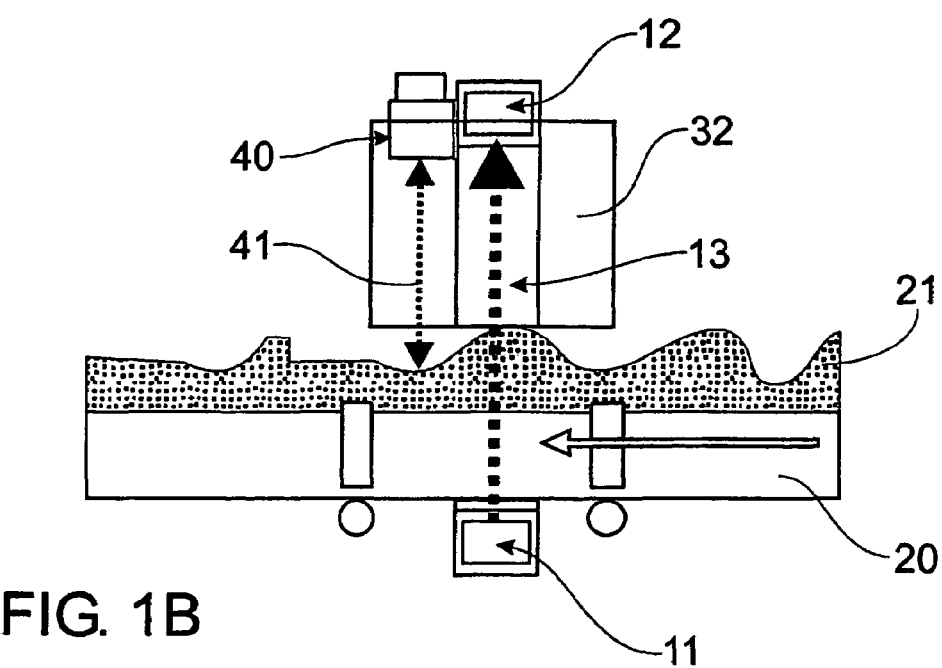
Figure 2A:
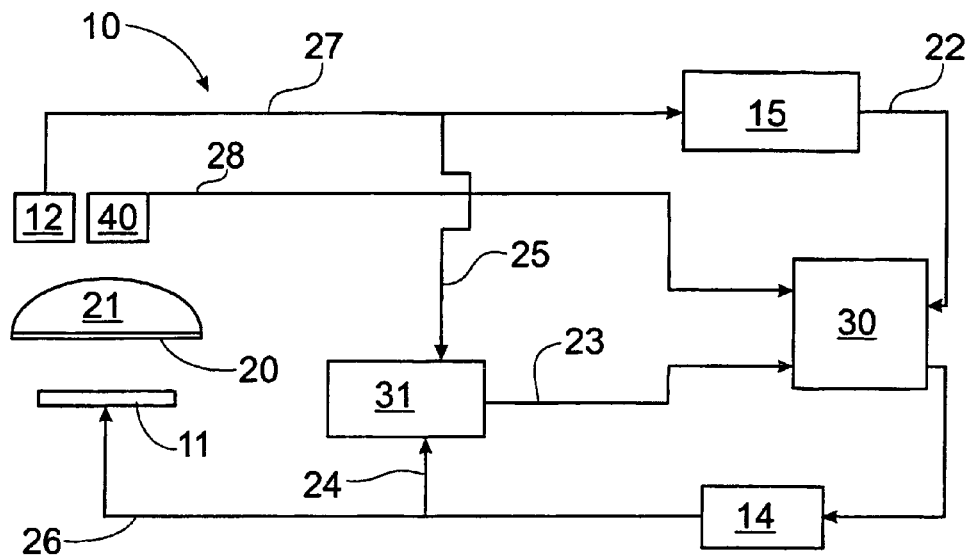
FIG. 2A shows a schematic diagram of an apparatus for measuring an amount of a component in a sample on a conveyor belt.

FIGS. 1A and 1B show a general representation of an apparatus 10 for measuring a component in a sample comprising a transmitting antenna 11, receiving antenna 12, an ultra-sonic apparatus 40 (located behind receiving antenna 12) and an electronics control cabinet 32 that houses a processor 30 shown in FIG. 2A. A sample 21 located on a conveyer belt 20 is shown being analysed by apparatus 10. A white arrow shown on conveyer belt 20 in FIG. 1B indicates direction of movement of the conveyer belt 20 and sample 21 located thereon.

FIG. 1A shows an end view of apparatus 10 transmitting a microwave signal 13 from transmitting antenna 11. The microwave signal is received by a receiving antenna 12 located above the sample 21. Ultra-sonic apparatus 40 is located behind receiving antenna 12 and is more clearly seen in FIG. 1B, which shows a side view of the apparatus 10 shown in FIG. 1A. Ultra-sonic apparatus 40 is located behind receiving antenna 12 (ie. after receiving antenna 12 relative to direction of movement of the conveyer belt 20). However, ultra-sonic apparatus 40 can alternatively be located in front of receiving antenna 12. Preferably, the ultra-sonic apparatus 40 and transmitting antenna 11 and receiving antenna 12 are located in substantially a same plane as shown so that the depth and microwave signals are measured for substantially a sample part of the sample 21.

An ultra-sonic signal 41 is shown as a double headed arrow. The ultra-sonic signal (eg. beam) measures sample bed depth. By measuring moisture content using the microwave signal and sample bed depth using the ultra-sonic signal, a percentage of moisture content can be determined. The processor 30 shown in FIG. 2A is a microprocessor (eg a computer) capable of receiving outputs from generated by respective devices of the apparatus 10 as described in more detail hereinafter. Processor 30 is located within an electronics control cabinet 32 that comprises a local display and keypad for operator interface. The display and keypad may comprise devices commonly known in the art, eg. touch screens, mouse cursor controllers, etc.

FIG. 2A shows a schematic representation of a preferred embodiment of the apparatus 10 comprising a microwave generator 14, transmitting antenna 11, receiving antenna 12, ultra-sonic apparatus 40, amplitude detector 15, microwave mixer 31 and processor 30. Also shown are generated microwave signal 26, received microwave signal 27, output 28 from ultra-sonic apparatus 40, output 22 from amplitude detector and output 23 from microwave mixer 31.

Figure 2B:
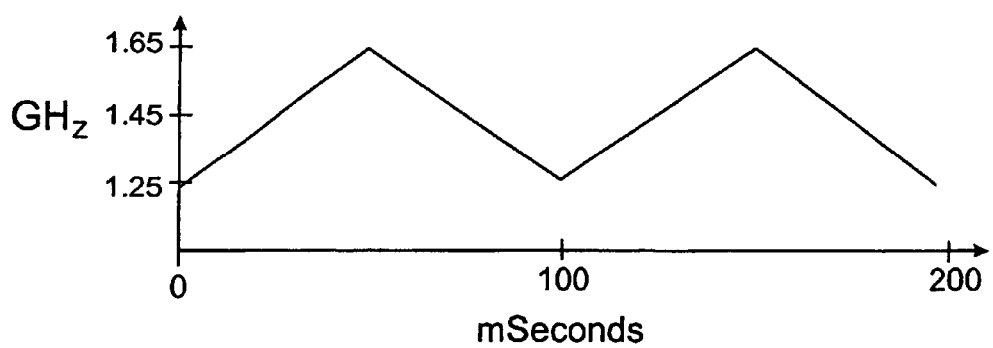
FIG. 2B shows an example of a transmitted continuous linearly sweeping microwave signal varying in frequency.

Shown in FIG. 2B is a transmitted signal shown as a continuous linearly sweeping microwave signal that varies in frequency inclusive from 1.25 GHz to 1.65 GHz in a preferred "saw tooth" pattern. Continuous linearly sweeping signal refers to frequency variations (ie. sweep) through a predetermined frequency range. As shown in FIG. 2B, a continuous linearly sweeping signal appears as a "saw tooth" pattern sweeping through a range inclusive of 1.25 GHz to 1.65 GHZ. This is distinct from a discontinuous signal that refers to one or more discrete single frequencies, for example, 1.0 GHz, 1.2 GHz and 1.4 GHz. The continuous linearly sweeping signal varying in frequency provides the advantages over apparatus that measure only a discrete single frequency as described herein.

Figure 2C:
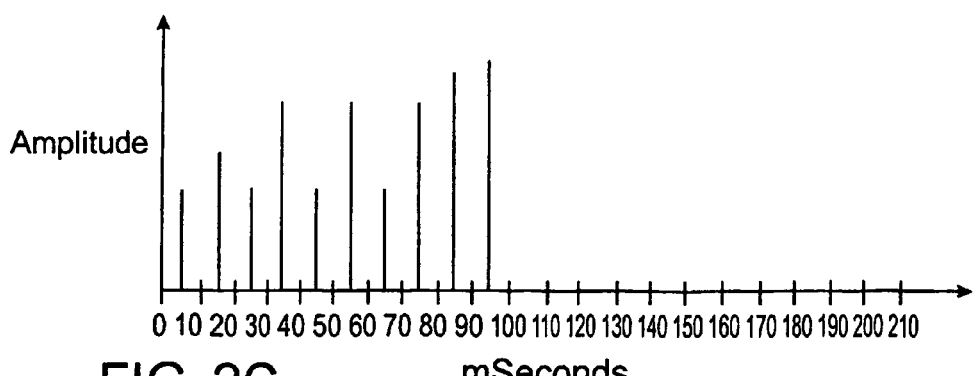
FIG. 2C shows an example of a received signal in a form of random stratified sampling.

FIG. 2C shows a received signal as measured attenuation of amplitude (ie. microwave power level) by Random Stratified Sampling. As discussed herein, a phase shift in microwave signal may also be measured using Random Stratified Sampling. Additional benefits of measuring by Random Stratified Sampling include improved accuracy of estimating actual free moisture content as discussed herein.

The apparatus 10 comprises a microwave generator 14 that is capable of generating a continuous linearly sweeping microwave signal of varying frequency. The frequency can be varied within any suitable range as a person skilled in the art could determine depending on the component and/or sample to be analysed. Preferably, the frequency is varied between about 0.10 GHz to 4.00 GHz for measuring, for example, water and/or carbon within the sample 21. However, a more preferred frequency range is inclusive of 1.25 GHz to 1.65 GHz. The microwave signal repeatedly cycles within a selected range, for example, increasing from 1.25 GHz to 1.65 GHz then decreasing to 1.25 GHz and so on in a "saw tooth" fashion as shown in FIG. 2. Microwave sweep generators known in the art would be suitable for use with the moisture analyser 10, including for example, a klystron source, a Gunn diode or preferably a YIG source (ie. a Yttrium Iron Garnet crystal). The generated microwave signal is sent to the transmit antenna 11 as shown in FIG. 2A.

A limitation of previous microwave analysers using attenuation is that they use set frequencies, or a number of discrete frequencies. The inventor has discovered that these known methods are less accurate due at least in part to a changing bulk density and thickness of the sample being measured. The present invention is an improvement over these known analysers by transmitting a continuous microwave signal that is linearly sweeping. Although the invention is useful with measuring component(s) of a sample on a conveyer belt, it will be appreciated that the sample need not be located on a conveyer belt and that the sample may be stationary.

The apparatus 10 has two (2) antennas 11 and 12; however, more than two (2) antenna may be used. A transmitting antenna 11 is located below sample 21 shown on conveyor belt 20. Transmitting antenna 11 transmits a microwave signal that is capable of passing through sample 21 and conveyer belt 20. A receiving antenna 12 is located above the sample 21 for receiving the microwave signal transmitted by transmitting antenna 11. It will be appreciated that the location of transmitting antenna 11 and receiving antenna 12 can be other than shown, for example the locations can be reversed. The location of the antennas need only be such that the transmitting antenna 11 can transmit a microwave signal at least partially through the sample 21 and the receiving antenna 12 can receive the transmitted microwave signal as a received signal after passing through at least part of the sample 21. The transmitting antenna 11 and receiving antenna 12 may be located at any suitable angle relative to the sample, including for example 90°, 80°, 45° or 20°. The distance of the transmitting antenna 11 is preferably close to the sample 21, such that the distance is less than the wavelength of the microwave signal. The respective antennas 11 and 12 can be any suitable antenna, for example horn antenna and dielectric rods as are known in the art.

The apparatus 10 also comprises an amplitude detector 15 capable of recording amplitude (eg. power levels) of the microwave signal received 27 by receiving antenna 12. Suitable amplitude detectors include those known in the art, for example, detector log video amplifiers DLVA. The amplitude is then transmitted to processor 30 as shown in FIG. 2A as an output 22, which may for example, be an analogue voltage output or a video output. In a preferred form, the output 22 is a simple five Volt to zero Volt analogue signal whereby five Volts indicates a highest amplitude and zero Volts indicates a lowest amplitude. The amplitude detector 15 is one form of a microwave analyser. It will be appreciated that in one embodiment, the microwave analyser may comprise both the microwave mixer and the amplitude detector.

The amplitude is preferably not recorded in a continuous fashion, but rather is preferably recorded by Random Stratified Sampling, as shown in FIG. 2C. Random Stratified Sampling is a process of sampling randomly between regular intervals. This is preferable to even time based sampling as unpredictable periodic effects can be eliminated. By using this sampling method an effect of signal reflection and superimposing, which is a result of varying bulk density and depth of material, can be reduced by a factor of 5.

Signal reflection and superimposing in relation to the present invention relates to when a microwave signal is transmitted into a dense medium (eg. sample), some of the microwave energy is reflected, some absorbed and some transmitted. The transmitted signal is measured for determining an amount of a component of a sample, for example water (moisture content) and/or carbon. However, the reflected signal can interfere with the signal that is being transmitted from the transmitting antenna. This interference can take a form on annulling or superimposing the transmitted signal. This is undesirable and a problem that is evident with known microwave moisture analysers that used a single frequency or discrete frequencies. By linearly sweeping the transmitted microwave signal over a broad bandwidth (eg. range of frequencies) and also sampling the signal using the Random Stratified Sampling technique, errors introduced by signal reflection and superimposing can be reduced. This is a major improvement and novel approach compared to previous methods using discrete frequencies.

Ultra-sonic apparatus 40 measures and records a depth of the sample 21 and generates an output signal 28. This ultra-sonic output signal 28 is also transmitted to the processor 30 as shown in FIG. 2A. Ultra-sonic apparatus that are known in the art are suitable for use with the invention, for example a Miltronics "Probe". Other methods for measuring sample depth may be used, for example nuclear digital density gauges. However, the ultra-sonic apparatus 40 is preferred when the sample has a varied depth and is located on a conveyor.

It will be appreciated that the apparatus in one form need not comprise an electronic means for determining sample depth. For example, if the apparatus is analysing a sample having a fixed depth, the sample depth may be determined using any suitable means known in the art, for example physically measuring the sample using a measuring device such as a measuring stick or ruler. A fixed depth may also occur if the sample is moving along a conveyor and a cutting surface or leveling surface is located above the sample to cut or level the sample to a fixed depth before analysis. For example, the sample may be a material such as flour, sugar, finely crushed ore and the like. Accordingly, for such embodiment, the value for sample depth may be input into an equation as a fixed value and calculated by the processor 30 to determine the amount of the component in the sample. For such an embodiment it will be appreciated that the apparatus may not need to comprise a means for measuring depth as part of the apparatus per se.

A sample 21 located between the transmitter and receiver (eg. between the transmitting and receiving antenna) will change the velocity of the received signal. This change in the velocity of the received signal 27 when compared with the velocity of the generated signal 26, or transmitted signal 13 (which typically remains substantially constant), will cause an output 23 of mixer 31 to also change. Accordingly, the change microwave velocity may be determined by microwave mixer 31 that measures a phase shift in the generated signal 26 (transmitted signal 13) and received microwave signal 27. The microwave mixer 31 is one form of a microwave analyser. Commercially available microwave mixers such as, Marki type mixers, are suitable for use with the invention.

Microwave mixer 31 receives at least a portion of the generated signal 24 and at least a portion of the received signal 25 and provides a measure of microwave velocity by measuring a phase shift in the respective signals. Microwave velocity is determined by measuring the change in the output 23 of the mixer 31. The output 23 of the mixer 31 is preferably an oscillating voltage. By measuring the DC bias of this oscillating voltage, a measure of the change in velocity or phase shift can be determined. The change in the DC bias is proportional to the change in velocity of the transmitted microwave signal and hence provides a measure of the change in the overall dielectric constant of the material between the two antennas 11, 12. This signal 23 is then transmitted to the processor 30. This DC bias can also be measured using the Random Stratified Sampling method as described herein. It will be appreciated that velocity and phase shift are directly proportional to each other, accordingly either may be measured.

Apparatus 10 is well suited for detecting an amount of at least one component, such as water and/or carbon content, of a sample 21 moving on a conveyor belt 20 because microwave signals can be transmitted continuously through the sample 21 as it moves along the conveyor belt 20. Accordingly, if the water and/or carbon content varies in the sample 21, an error in detecting water and/or carbon content is reduced. Although apparatus 10 in a preferred embodiment is used to detect at least one component, eg water and/or carbon content, in a sample moving along a conveyor belt, apparatus 10 can also be used to measure an amount of a component in a stationary sample. The sample can be any suitable sample that is substantially transparent to microwave signals. The sample can have a varying thickness or a constant thickness. The sample may be crushed (eg. as for coal) or uncrushed. Conveyor belt 20 is substantially microwave transparent and may be made of a material such as a synthetic plastic, including polypropylene, polyvinyl chloride. Conveyor belts for minerals (eg. coal) may have a PVC layer laminated with a wear resistant layer, such as chlorinated polyethylene or "Neoprene"®.

An amount of a component in a sample 21 can be determined using the apparatus 10 by measuring attenuation of microwave amplitude (eg. power level) and ultrasonic bed depth, without measuring microwave velocity. Alternatively, an amount of a component in a sample may determined by measuring microwave velocity, which affects a phase shift, and ultrasonic bed depth, without measuring a change in attenuation. When only amplitude or velocity is measured, the variable not measured is set to zero in an equation shown in the examples. Further, in a preferred form of the invention, an amount of a component in a sample may be determined by measuring microwave attenuation, microwave velocity and ultrasonic bed depth, which in some applications may improve accuracy of determining moisture content.

Measuring Attenuation, Velocity and Sample Depth

Measurement (in dB) of the power level (ie. amplitude) of both an empty conveyor belt and a sample laden conveyor belt is used to derive attenuation of microwave power level caused by the sample, which is being analysed.

Attenuation of amplitude=(Power level measured on laden belt)-(Power level measured on empty belt).

Like wise the measurement of respective velocities of an empty conveyor belt and a sample laden conveyor belt is used to derive a change in velocity caused by the sample being analysed.

Microwave velocity=(Laden belt velocity)-(Empty belt velocity).

The depth of material upon the conveyor belt is measured by subtracting the depth of a sample on a laden belt from depth of an empty belt. Depth of material is estimated using an ultra-sonic measuring apparatus, however other means as described herein may also be used.

Depth of Sample=(Depth of sample on a laden belt)-(depth of material on a empty belt).

Calculating Moisture Content

The following equation is preferably used to predict moisture content in a sample.

$$\text{Moisture content} = M0 + M1^*(\text{Atten/Depth of sample}) + M2^*(\text{Velocity/Depth of sample}) + M3^*(\text{Velocity/Depth of material})^2 + M4^*(\text{Atten/Depth of sample})^2$$

Where M0, M1, M2, M3 and M4 are calibration coefficients that are dependent upon an application and sample analysed. These values may be determined by performing a simple linear regression of the respective variables (Atten/Depth of sample), (Velocity/Depth of sample), (Velocity/Depth of material)$^2$ and (Atten/Depth of sample)$^2$ against experimental (e.g. laboratory determined) moisture value determined using methods known in the art. Such methods include weighing a sample, drying the sample to remove water therefrom and weighing the sample again to determine an amount of water that was present in the sample. The abovementioned variables are selected as a X-range and standard laboratory results are selected as the Y-range. Such analysis may include use of computer programs such as Excel and Lotus 123. The values of M0, M1, M2, M3 and M4 may likewise be determined for any other component to be analysed in a selected sample.

In order that the invention may be readily understood and put into practical effect, particular preferred embodiments will now be described by way of the following non-limiting example.

EXAMPLE 1

Water Content Analysis for Sugar

Apparatus Set-up and Assessment

The sample analyser as described in FIGS. 1 and 2 was used for determining moisture content within refined sugar. The analyser was left to stabilise after power-up for a period of 1 hour for heated enclosures to reach a stable temperature (this provides stability for the microwave components). The generated microwave signal was transmitted as a continuous linearly sweeping signal varying in frequency from about 1.25 GHz to about 1.65 GHz. The output of the microwave ("M/W") attenuation of amplitude, velocity, and ultrasonic bed depth are transferred to a standard industrial type Programmable Logic Controller (PLC), where by the results are recorded from the appropriate addresses. Any suitable PLC common in the art may be used.

M/W attenuation, velocity, and ultrasonic bed depth is measured for an empty conveyor belt.

A sample of material is placed onto a running conveyor. For a period of 15 minutes the average M/W attenuation, velocity, and ultrasonic bed depth are measured. During this same period a sample of the material is taken from the moving conveyor and sent to a laboratory for the measurement of % Total Moisture.

The following values are used:
Attenuation (atten) of amplitude=(M/W attenuation upon laden conveyor)-(M/W attenuation upon empty conveyor belt)
Microwave velocity=(M/W velocity upon laden conveyor)-(M/W velocity upon empty conveyor belt)
Bed Depth=(ultrasonic bed depth upon laden conveyor)-(ultrasonic bed depth upon empty conveyor belt)

Approx 15 samples were taken over a varying moisture range for calibration. The following data is data obtained by a simulated trial.

Results

The data set for a moisture analysis of refined sugar is shown in tables 1 and 2. A comparison between moisture values determined using the apparatus of the present invention and a standard laboratory method is shown graphically in FIG. 3, with an $R^2$ value of 0.9959. Standard laboratory methods are well known in the art. For example, to assess water content the sample may be weighed before and after drying of the sample to determine water content.

A simple linear regression was performed using the three (3) measurements (ie attenuation, velocity and sample depth) determined by the abovementioned apparatus and correlated with experimental laboratory moisture values as shown in table 1. The regression output data is shown in table 2.

Gauge predicted moisture is calculated using the following equation:

$$\text{Moisture content} = M0 + M1^*(\text{Atten/Depth of sample}) + M2^*(\text{Velocity/Depth of sample}) + M3^*(\text{Velocity/Depth of sample})^2 + M4^*(\text{Atten/Depth of sample})^2$$

Figure 3:
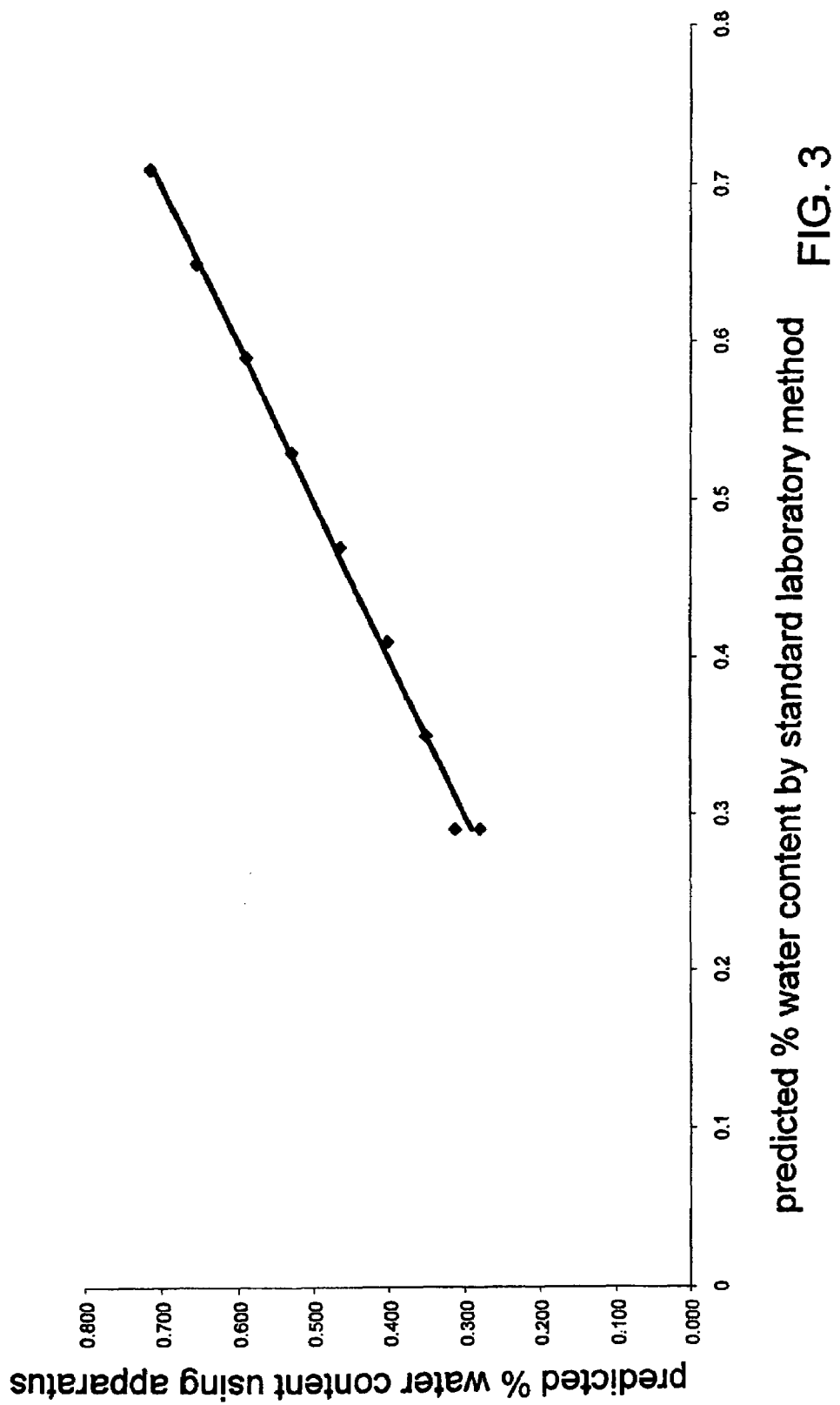
FIG. 3 is a graph showing prediction of moisture content of sugar using the apparatus of the invention versus experimental moisture content.

In this example, the following values were used as calculated from the regression curve in FIG. 3 and data shown in table 2.

M0=0.475, M1=208.117, M2=−0.04454, M3=0 and M4=0
M3 and M4 values are used if there is a non-linear relationship with one of the variables: (Atten/Depth of sample) or (Velocity/Depth of sample).

EXAMPLE 2

Water Content Analysis for Peanuts

Figure 4:
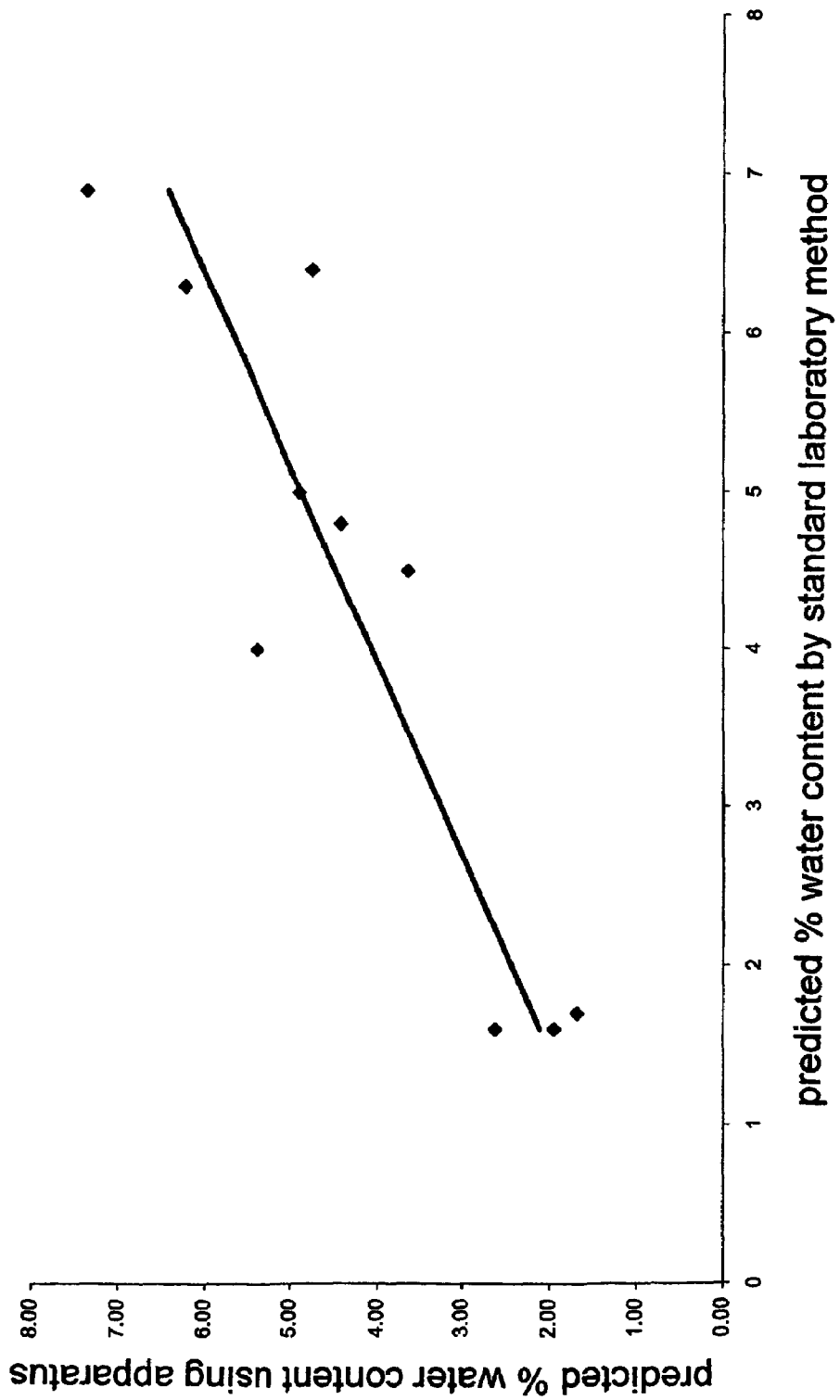
FIG. 4 is a graph showing prediction of moisture content of peanuts using the apparatus of the invention versus experimental moisture content.

A similar analysis as described in Example 1 was performed on Kingaroy peanut samples using the same frequency range and same equation as for Example 1 with the variable inputs for the equation as shown in Tables 3 and 4. A graph comparing the calculated versus experimental data is shown in FIG. 4.

EXAMPLE 3

The use of Microwave Apparatus for the Determination of Percent Carbon in Flyash At Coal Fired Power Stations, large amounts of ash (commonly referred to as flyash) are produced from the combustion of coal. This ash is transported by large ducts directly from the power station boilers to collections points within the power station. Within the ash there is a small component of unburnt carbon. The measurement of this unburnt carbon can be used in controlling the efficiency of the boilers.

It has been found that using the apparatus of the present invention and locating the respective microwave transmitter and receiver at either side of the duct and transmitting the microwave signal across the duct (approximately a 5 metre span), it is possible to derive a percent of unburnt carbon within the ash burden. The respective transmitter and receiver may be placed at any suitable angle relative to the duct, however, it is preferred that the receiver is located so as to be capable of receiving a majority of the transmitted signal.

This measurement of carbon in the ash is possible in part because there is negligible moisture within the duct. Accordingly, a large dielectric caused by moisture variation is substantially removed and almost non-existent. By examining attenuation and phase shift signal a difference in dielectric constant between the percent carbon within the flyash can be determined. An equation used to determine carbon percentage is essentially the same as the equation used to determine water content, however, when determining carbon percentage in this example, the depth reading will be constant as the antenna operated on fixed geometry.

Table 5 shows data comparing percent carbon determined by laboratory experimentation and determined by using the apparatus of the invention. The frequency of the microwave signal was varied from about 1.25 GHz to about 1.65 GHz. The data in Table 5 is graphically illustrated in FIG. 5, wherein the laboratory experimental data is shown as diamonds (♦) and the data determined by the invention is shown as squares (□).

FIG. 6 shows a graph of data comparing percent carbon determined by laboratory experimentation and determined by using the apparatus of the invention. A line shown in FIG. 6 has a value of y=0.8606+0.733 and $R^2$=0.8606.

The data from FIGS. 5 and 6 were used to calculate the calibration coefficients as described above via simple linear regression. Percent carbon content was determined using the same equation shown in Example 1.

It is understood that the invention described in detail herein is susceptible to modification and variation, such that embodiments other than is those described herein are contemplated which nevertheless falls within the broad scope of the invention.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

The disclosure of each patent and scientific document, computer program and algorithm referred to in this specification is incorporated by reference in its entirety.

TABLE 1

| Lab % Moist | Measured Sample Variables | | | | | Gauge Predicted % Moisture |
|---|---|---|---|---|---|---|
| | Attn | Velocity | Sample Depth | Atten/Sample depth | Velocity/ Sample depth | |
| 0.29 | 1.354 | 8782.2 | 604 | 0.002241722 | 14.54006623 | 0.279 |
| 0.29 | 1.452 | 8782 | 602 | 0.00241196 | 14.58803987 | 0.313 |
| 0.35 | 1.5649 | 8786 | 598 | 0.00261689 | 14.69230769 | 0.351 |
| 0.41 | 1.71 | 8787 | 597 | 0.002864322 | 14.71859296 | 0.401 |
| 0.47 | 1.89 | 8789 | 601 | 0.003144759 | 14.62396007 | 0.464 |
| 0.53 | 2.08 | 8790 | 620 | 0.003354839 | 14.17741935 | 0.528 |
| 0.59 | 2.25 | 8791.3 | 598 | 0.003762542 | 14.70117057 | 0.589 |
| 0.65 | 2.438 | 8792.5 | 601 | 0.004056572 | 14.62978369 | 0.653 |
| 0.71 | 2.614 | 8792 | 604 | 0.004327815 | 14.55629139 | 0.713 |

TABLE 2

| Regression Output: | | |
|---|---|---|
| Constant | | 0.475187 |
| Std Err of Y Est | | 0.011373 |
| R Squared | | 0.995924 |
| No. of Observations | | 9 |
| Degrees of Freedom | | 6 |
| | Atten/Bed depth | Vel/Bed depth |
| X Coefficient(s) | 208.117 | −0.04554 |
| Std Err of Coef. | 5.469494 | 0.024566 |

TABLE 3

| Percent Moisture Experimental | Moisture prediction | Phase | Atten | Sample Depth | Phase/Sample Depth | Atten/Sample Depth | (Phase/Sample Depth)$^2$ | (Atten/Sample Depth)$^2$ | Percent Moisture Predicted |
|---|---|---|---|---|---|---|---|---|---|
| 6.9 | 7.34 | 4642.87 | 3.693 | 30 | 154.7623333 | 0.1231 | 23951.37982 | 0.01515361 | 7.344118772 |
| 4.8 | 4.40 | 4639.53 | 3.608 | 28 | 165.6975 | 0.128857143 | 27455.66151 | 0.016604163 | 4.395750125 |
| 1.6 | 1.94 | 4637.6 | 3.413 | 32 | 144.925 | 0.10665625 | 21003.25563 | 0.011375556 | 1.943040056 |
| 6.4 | 4.73 | 4647.4 | 3.567 | 31 | 149.916129 | 0.115064516 | 22474.84574 | 0.013239843 | 4.725075136 |
| 1.7 | 1.68 | 4844 | 3.396 | 30 | 154.8 | 0.1132 | 23963.04 | 0.01281424 | 1.678283675 |
| 5 | 4.88 | 4651.9 | 3.576 | 30 | 155.0633333 | 0.1192 | 24044.63734 | 0.01420864 | 4.878647633 |
| 6.3 | 6.20 | 4652.31 | 3.687 | 32 | 145.3846875 | 0.11521875 | 21136.70736 | 0.01327536 | 6.204476668 |
| 1.6 | 2.62 | 4648.74 | 3.486 | 29 | 160.3013793 | 0.120206897 | 25696.53221 | 0.014449698 | 2.616534816 |
| 4 | 5.39 | 4649.6 | 3.606 | 31 | 149.9870968 | 0.116322581 | 22496.1292 | 0.013530943 | 5.391636601 |
| 4.5 | 3.62 | 4648.53 | 3.507 | 30 | 154.951 | 0.1169 | 24009.8124 | 0.01366561 | 3.622436518 |

Regression Output
| | | |
|---|---|---|
| Constant | | −213.7458091 |
| Std Err of Y Est | | 1.187277984 |
| R Squared | | 0.811425914 |
| No. of Observations | | 10 |
| Degrees of Freedom | | 5 |
| X Coefficient(s) | 3.166830274 | −403.1009844 | −0.011766751 | 4120.176087 |
| Std Err of Coef. | 4.592100619 | 3315.234895 | 0.01501512 | 14290.27003 |

TABLE 4

Regression Output:

| | |
|---|---|
| Constant | −72.9066 |
| Std Err of Y Est | 0.775114 |
| R Squared | 0.871404 |
| No. of Observations | 10 |
| Degrees of Freedom | 8 |
| X Coefficient(s) | 18.65041 |
| Std Err of Coef. | 2.533074 |

TABLE 5

| Experimental laboratory values from a manual sampler (% carbon) | Determined via apparatus (% carbon) |
|---|---|
| 5.1 | 3.32 |
| 4.9 | 3.32 |
| 4.9 | 4.42 |
| 5.4 | 4.75 |
| 4.4 | 4.72 |
| 4.9 | 5.53 |
| 4.9 | 5.47 |
| 5.7 | 5.26 |
| 5.9 | 5.96 |
| 4.9 | 6.27 |
| 5.0 | 6.22 |
| 5.8 | 6.42 |
| 5.7 | 6.47 |
| 6.3 | 6.29 |
| 6.3 | 6.33 |
| 7.4 | 6.60 |
| 8.0 | 6.42 |
| 10.8 | 9.25 |
| 10.3 | 9.04 |
| 10.3 | 8.95 |
| 8.3 | 8.87 |
| 8.5 | 8.84 |
| 6.2 | 5.48 |
| 6.5 | 7.26 |
| 7.9 | 7.35 |
| 9.3 | 7.76 |
| 9.7 | 8.36 |
| 9.4 | 8.78 |
| 8.9 | 8.84 |
| 7.5 | 8.87 |
| 7.7 | 8.22 |
| 6.6 | 7.77 |
| 3.8 | 4.46 |
| 4.1 | 6.20 |
| 4.8 | 3.79 |
| 4.1 | 3.99 |
| 3.9 | 3.88 |
| 3.0 | 4.04 |
| 4.2 | 4.58 |
| 3.4 | 4.82 |
| 4.6 | 4.97 |
| 3.8 | 5.21 |
| 2.9 | 3.29 |
| 2.9 | 2.91 |
| 2.8 | 3.18 |
| 2.9 | 2.68 |
| 3.3 | 2.77 |
| 2.6 | 2.83 |
| 3.0 | 2.69 |
| 2.9 | 2.56 |
| 3.0 | 2.65 |
| 2.8 | 2.49 |
| 2.9 | 2.56 |
| 2.9 | 2.53 |
| 2.6 | 2.81 |
| 2.9 | 2.58 |
| 2.8 | 2.76 |
| 3.2 | 2.91 |
| 3.1 | 3.66 |
| 2.8 | 4.20 |

The invention claimed is:

1. A sample analysis apparatus that measures an amount of water in a sample comprising:
(i) a microwave generator that generates a continuous linearly sweeping microwave signal varying in frequency;
(ii) a microwave transmitter that transmits the generated signal;
(iii) a microwave receiver that receives the transmitted signal;
(iv) at least one microwave analyser that generates an output signal, which is operatively connected to the microwave transmitter and to the microwave receiver; said output signal indicating a phase shift and/or an attenuation of amplitude of the microwave signal when comparing the generated signal and the received signal, and the at least one microwave analyser is capable of measuring the phase shift and/or attenuation of the amplitude of the microwave signal by random stratified sampling of the received signal;

(v) means for determining a depth of the sample located between said microwave transmitter and said microwave receiver; and (vi) a processor that determines the amount of the water in the sample from the depth and said output signal using the equation:

Moisture content=$M0+M1$*(Attenuation/Depth of sample)+$M2$*(Velocity/Depth of sample)$M3$* (Velocity/Depth of sample)$^2$+$M4$*(Attenuation/Depth of sample)$^2$; wherein Attenuation=(amplitude measured with sample)−(amplitude measured without sample);

Velocity=(microwave velocity measurement with sample)−(microwave velocity measurement without sample); and Depth of sample=(Depth with sample)−(depth without sample); and M0, M1, M2, M3 and M4 are calibration coefficients determined by performing a simple linear regression of variables: (Attenuation/Depth of sample), (Velocity/Depth of sample), (Velocity/Depth of sample)$^2$ and (Attenuation/Depth of sample)$^2$ against experimentally determined values for water.

2. The apparatus of claim 1 wherein said means for determining a depth of the sample comprises a sample depth analyser that measures depth of the sample.

3. The apparatus of claim 2 wherein the sample depth analyser is an ultra-sonic transmitting device.

4. The apparatus of claim 1 wherein the continuous linearly sweeping microwave signal varies in frequency between a range of about 0.10 GHz to 4.00 GHz.

5. The method of claim 4 wherein the continuous linearly sweeping microwave signal varies in frequency between a range inclusive of 1.25 GHz to 1.65 GHz.

6. The apparatus of claim 1 wherein the transmitter and receiver comprise respective antennas.

7. The apparatus of claim 1 wherein the microwave analyser comprises a microwave mixer that measures phase shift by receiving a portion of the transmitted signal and a portion of the received signal.

8. The apparatus of claim 7 wherein the microwave mixer generates an output signal comprising an oscillating voltage with a DC bias and frequency wherein a change in the DC bias or frequency is proportional to a change in velocity of the transmitted signal and provides a measure of a change in overall dielectric constant of water in the sample.

9. The apparatus of claim 1 wherein the microwave analyser comprises a microwave amplitude detector that measures an amplitude of the received signal.

10. The apparatus of claim 1 wherein the random stratified sampling is performed using an algorithm programmed into the processor.

11. The apparatus of claim 1 wherein the processor is a microprocessor.

12. The apparatus of claim 1 wherein M0=0.475, M1=208.117, M2=−0.4454, M3=0 and M4=0.

13. Use of the apparatus of claim 1 to determine an amount of water in a sample.

14. Use of the apparatus of claim 1 where the sample is an ore, mineral, coal, flyash, nickel ore, alumina; chromium ore, wood chip; bulk food, textile, chemical, food product, sugar, pasta, coffee, peanuts, wheat, barley, beef jerky, kitty litter, paper, polystyrene or plastic.

15. A method for measuring an amount of water in a sample including the steps of:

(1) generating a continuous linearly sweeping microwave signal varying in frequency;

(2) transmitting the generated signal;

(3) receiving a received signal;

(4) measuring and analysing the generated signal and the received signal and generating an output signal; said output signal indicating phase and/or amplitude differences between the generated signal and the received signal;

(5) measuring a depth of the sample to provide a sample depth measurement; and (6) processing the output signal and the sample depth measurement to determine the amount of water in the sample using the equation:

Moisture content=$M0+M1$ *(Attenuation/Depth of sample)+$M2$*(Velocity/Depth of sample)+$M3$* (Velocity/ Depth of sample)$^2$+$M4$*(Attenuation/Depth of sample)$^2$; wherein Attenuation=(amplitude measured with sample)−(amplitude measured without sample);

Velocity=(microwave velocity measurement with sample)−(microwave velocity measurement without sample); and Depth of sample=(Depth with sample)−(depth without sample); and M0, M1, M2, M3 and M4 are calibration coefficients that are determined by performing a simple linear regression of the variables: (Attenuation/Depth of sample), (Velocity/Depth of sample), (Velocity/Depth of sample)$^2$ and (Attenuation/Depth of sample)$^2$ against experimentally determined values for water.

16. The method of claim 15 wherein the continuous linearly sweeping microwave signal varies in frequency between a range of about 0.10 GHz to 4.00 GHz.

17. The method of claim 16 wherein the continuous linearly sweeping microwave signal varies in frequency between a range inclusive of 1.25 GHz to 1.65 GHz.

18. The method of claim 17 wherein the steps of transmitting and receiving signals is by respective antennas.

19. The method of claim 15 wherein phase shift is measured by a microwave mixer that receives a portion of the generated signal and a portion of the received signal.

20. The method of claim 19 wherein the output signal comprises an oscillating voltage with a DC bias that is proportional to both a change in microwave velocity and phase shift.

21. The method of claim 15 wherein attenuation of an amplitude of the generated signal is measured by an amplitude detector.

22. The method of claim 15 wherein the phase and/amplitude differences are measured by random stratified sampling of the received signal.

23. The method of claim 22 wherein the random stratified sampling is performed using an algorithm within a processor.

24. The method of claim 15 wherein the step of measuring a depth of the sample is by an ultra-sonic means.

25. The method of claim 15 wherein the processing is performed by a microprocessor.

26. The method of claim 15 wherein M0=0.475, M1=208.117, M2=−0.04454, M3=0 and M4=0.

* * * * *